(12) United States Patent  
Shepard

(10) Patent No.: US 9,157,878 B2  
(45) Date of Patent: Oct. 13, 2015

(54) SYSTEM AND METHOD FOR DETECTING ABERRATIONS IN A CONDUIT

(71) Applicant: THERMAL WAVE IMAGING, INC., Ferndale, MI (US)

(72) Inventor: Steven M. Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 291 days.

(21) Appl. No.: 13/648,806

(22) Filed: Oct. 10, 2012

(65) Prior Publication Data

US 2013/0091927 A1    Apr. 18, 2013

Related U.S. Application Data

(60) Provisional application No. 61/546,890, filed on Oct. 13, 2011.

(51) Int. Cl.
*G01N 25/72* (2006.01)
*G01N 19/08* (2006.01)
*G01M 15/14* (2006.01)

(52) U.S. Cl.
CPC ............. *G01N 25/72* (2013.01); *G01M 15/14* (2013.01); *G01N 19/08* (2013.01)

(58) Field of Classification Search
CPC ....... G01M 15/14; G01N 25/72; G01N 19/08; G01N 2203/0062
See application file for complete search history.

(56) References Cited

U.S. PATENT DOCUMENTS

| | | | |
|---|---|---|---|
| 5,308,162 | A | 5/1994 | Amano et al. |
| 5,333,501 | A | 8/1994 | Okada et al. |
| 5,531,099 | A | 7/1996 | Russo |
| 6,453,247 | B1 | 9/2002 | Hunaidi |
| 2002/0062693 | A1* | 5/2002 | Gorman et al. ................. 73/592 |
| 2006/0032606 | A1 | 2/2006 | Thybo et al. |
| 2008/0107147 | A1 | 5/2008 | Kollgaard et al. |
| 2009/0223284 | A1 | 9/2009 | Buhring |
| 2010/0206090 | A1* | 8/2010 | Stack ....................... 73/861.357 |

OTHER PUBLICATIONS

International Search Report for Application PCT/US2012/059807 dated Jan. 7, 2013.

* cited by examiner

*Primary Examiner* — Paul West
(74) *Attorney, Agent, or Firm* — Honigman Miller Schwartz and Cohn LLP

(57) ABSTRACT

A system for detecting aberrations within a workpiece having a conduit with an input end and an output end is disclosed. The system comprises a fluid delivery device arranged proximate to input end of conduit to pass fluid into input end of the conduit, the fluid delivery device having one or more fluid controllers that control one or more conditions of the fluid passed thereby, a sensor having an input and an output, the input arranged proximate to output end of conduit to measure one or more conditions of the fluid experienced by input, a workpiece exciter situated to excite workpiece and a processor having an input connected to the output of sensor, the processor having a correlator to correlate any changed of the one or more conditions of the fluid experienced by input of sensor with an excitement of workpiece by sensor.

5 Claims, 4 Drawing Sheets

SYSTEM AND METHOD FOR DETECTING ABERRATIONS IN A CONDUIT

PRIORITY

This Application claims the benefit of U.S. Provisional Patent Application Ser. No. 61/546,890 filed on Oct. 13, 2011, which is entirely incorporated herein by reference.

TECHNICAL FIELD

This disclosure relates to systems and methods for identifying a presence of aberrations within an internal conduit of a workpiece.

BACKGROUND

Various techniques are used to identify cracks or other aberrations, located on or near, the external surfaces of a workpiece. For example, fluorescent penetrant methods aid a human operator in detecting small cracks, and eddy current instruments detect flaws at or near the surface that disrupt an induced magnetic field. These techniques, however, require direct access to the surface of the workpiece and they are not applicable to identifying aberrations that may exist on an internal surface or conduit of a workpiece. While optical imaging through a borescope is generally capable of the internal walls of conduit, in some structures the conduits may be too small and/or labyrinthine to allow passage of the probe.

In certain environments it may not only be desirable to identify the presence of aberrations located along the internal walls of a conduit, such identifications can be mission critical. For example, engine turbines often include multiple conduits that extend generally through a body. It is important to identify the presence of any aberrations, such as cracks or the like, that may reside along the walls of such one or more conduits. However, in instances where conduit walls are not directly accessible, many traditional inspection devices are ineffective for detecting some aberrations that may intersect the conduit walls. The inventor hereof has realized a system and method that facilitates identification of such aberrations in a timely and efficient manner.

SUMMARY

A system for detecting a presence of aberrations within a workpiece having a conduit with an input end and an output end is disclosed. The system comprises a fluid delivery device arranged proximate to input end of conduit to pass fluid into input end of the conduit, the fluid delivery device having one or more fluid controllers that control one or more conditions of the fluid passed thereby, a sensor having an input and an output, the input arranged proximate to output end of conduit to measure one or more conditions of the fluid experienced by input, a workpiece exciter situated to excite workpiece and a processor having an input connected to the output of sensor, the processor having a correlator to correlate any changed of the one or more conditions of the fluid experienced by input of sensor with an excitement of workpiece by sensor.

In an embodiment, the method comprises passing fluid through the intake end of the internal conduit at a generally constant temperature and at a generally constant velocity, equalizing a temperature of the workpiece with the generally constant temperature of the passing fluid, measuring the temperature of the fluid at the outtake end of the internal conduit, exciting the workpiece at a defined interval and identifying whether an aberration is present within the internal conduit based on the measured temperature in view of the defined interval. These and other features will be discussed herein.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
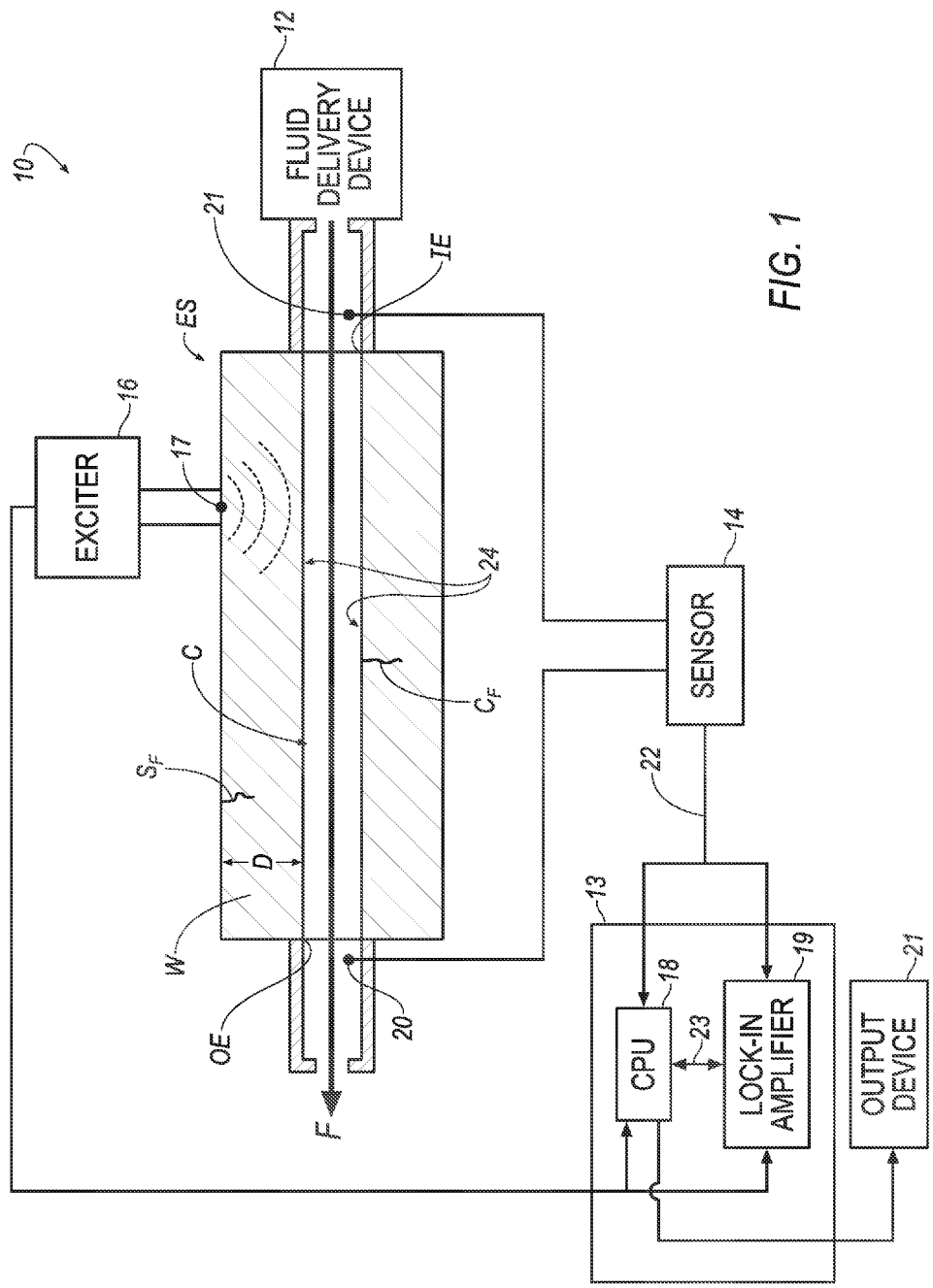
FIG. 1 depicts a cross-sectional diagram of a system for detecting aberrations within the conduit of a workpiece, according to an implementation.

Referring to FIG. 1, a cross-sectional illustration of a workpiece W is shown. As depicted, workpiece W includes inner walls 24 that define conduit C that extends through workpiece W between an input end IE and an output end OE of workpiece W. A system for detecting a presence of aberrations within the walls 24 of conduit C is also shown in FIG. 1 and is generally represented at 10. The type of aberrations that may be detected by system 10 include surface aberrations that may be present within the walls 24 of conduit C irrespective of whether the aberrations are directly viewable using line-of-sight techniques. Such aberrations may include surface fissures, cracks and the like Cf; however, the detection may not be limited to surface aberrations and the system may be used to detect other aberrations such as partial or complete blockages, etc. Additionally, within this disclosure, an exemplary workpiece W is generally metallic but it is to be understood that other workpiece compositions may be used and the scope of this disclosure should not be so limited thereby by the workpiece composition.

In an implementation, system 10 includes a fluid delivery device 12, a sensor 14, an exciter 16, a lock-in amplifier 19, an output device 21, and a processor 18. As depicted, fluid delivery device 12 is arranged proximate to input end IE of conduit C so as to deliver fluid F into input end IE of conduit C in the direction generally represented by the arrow that is identified in the illustration. Fluid delivery device 12 may also be a source of vacuum to draw fluid through conduit C. With continued reference to FIG. 1, sensor 14 may be arranged proximate to input end IE and output end OE of conduit C. Sensor is arranged and adapted to facilitate a measurement of one or more conditions of fluid F as it enters or egresses conduit C. Exciter 16 is located at a position that is external to workpiece W, and in an arrangement that facilitates exciter 16 to mechanically, thermally, or otherwise excite workpiece W, the purpose and detail of which will be further discussed hereinbelow. Fluid delivery device 12 is depicted pushing fluid F through conduit C but device 12 can also be an electric motorized vacuum pump which draws fluid F through conduit C.

According to an embodiment, fluid delivery device 12 may include one or more fluid controllers (not shown) that can control one or more conditions of fluid F that it delivers into intake end IE of conduit C. CPU 18 could function as one such fluid controller. For purposes of the discussion in this disclosure, fluid F is ambient air but one of ordinary skill in the art will appreciate that fluid F could be any fluid (i.e., gas or liquid) and the invention should not be so limited thereby. In an implementation, the one or more conditions generally controlled by fluid delivery device 12 may include the flow rate and/or the temperature of fluid F as it is delivered into input end IE of conduit C of workpiece W.

In an implementation, sensor 14 is an electronic sensor capable of out putting an electric signal proportional to its sensed input and includes one or more inputs 20, 21 and one or more outputs 22. Inputs 20, 21 of sensor 14 senses one or more conditions of fluid F as the fluid enters input end IE and/or exits output end OE of conduit C of workpiece W. In an implementation, and similar to the one or more conditions that can be generally controlled by fluid delivery device 12, the one or more conditions sensed by sensor 14 may include the temperature of fluid F as it enters IE of conduit C and/or exits the output end OE of conduit C of workpiece W, the velocity of fluid F, and the like. As an example, sensor 14 may be one or a combination of a thermocouple, a thermistor, a resistance temperature detector, a mass flow sensor, volume flow detector, infrared camera, velocity sensor and the like.

FIG. 1 depicts an arrangement whereby one or more outputs 22 of sensor 14 is connected to processor 18 lock-in amplifier 19, or both. In an implementation, processor 18 and lock-in amplifier are analog and or digital electronic devices capable of receiving, collecting, and interpreting electronically embodied information provided by sensor 14, the details of which will be discussed in connection with the operation of system 10 hereinbelow. At least one of processor 18, lock-in amplifier or both, comprise a detecting device 13 for detecting fluctuations in conditions in fluid F.

In an implementation, exciter 16 is a mechanical exciter. For example, exciter 16 may be a device that inputs vibrational energy to workpiece W thereby vibrating workpiece W. In a system, exciter 16 may be configured to excite workpiece W at a defined interval. In an embodiment, exciter 16 may be a sonic horn, an acoustic horn, or any type of device that may be used to transfer vibrational mechanical energy to an exterior surface ES of workpiece W. In an implementation, exciter 16 is connected to processor 18, lock-in amplifier 19, or both such that processor 18 and lock-in amplifier can collect information regarding the condition of exciter 16 and may control the activation of exciter 16 at defined intervals. Also, processor 18 and lock-in amplifier 19 can pass control and data therebetween along two-way bus 23.

Figure 2:
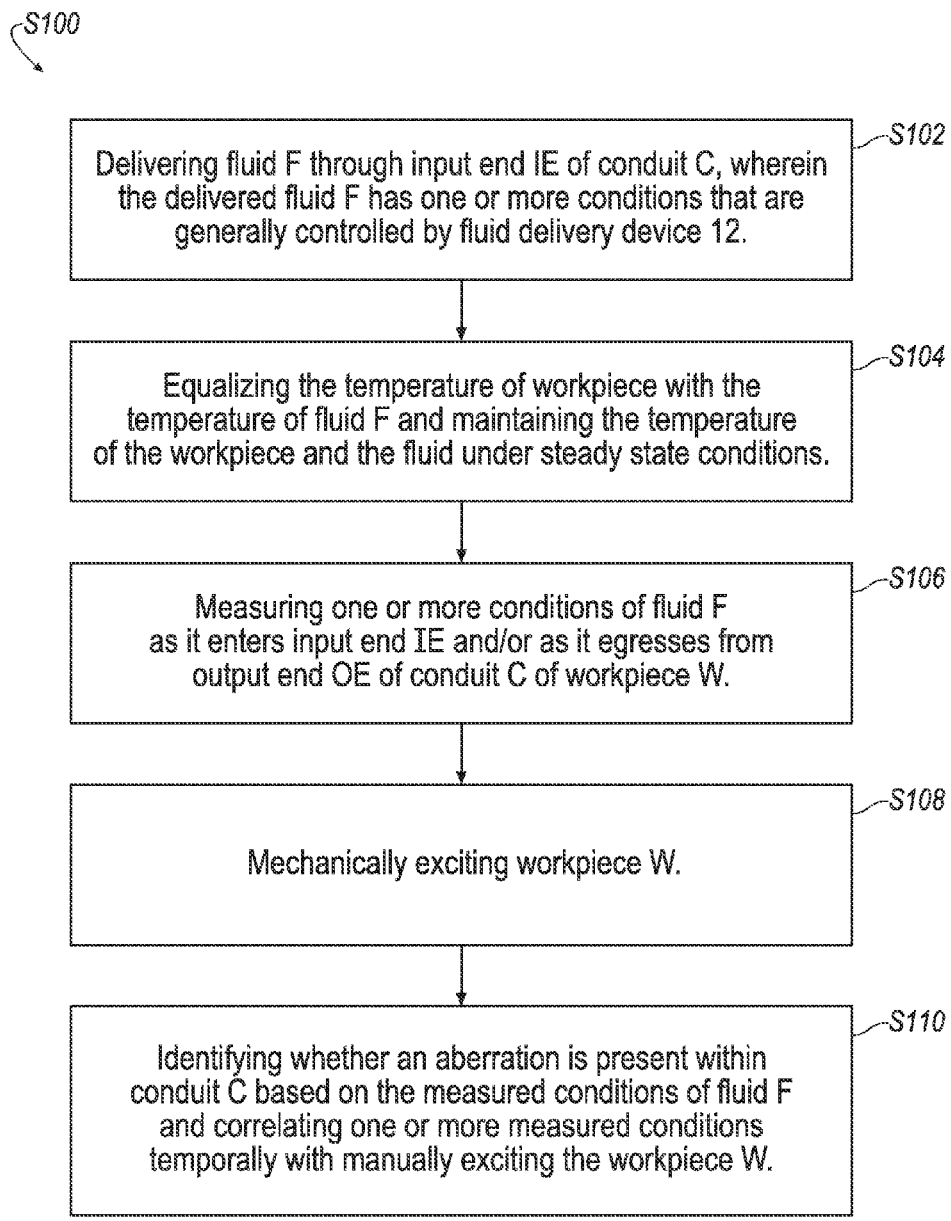
FIG. 2 depicts a method for detecting aberrations within the conduit of a workpiece, according to an implementation.

A method of operating system 10 to detect a presence of aberrations described above within conduit C will now be described. Such a method is exemplarily illustrated and referenced in FIG. 2 and shown at S100. In an implementation, method S100 comprises, at step S102, delivering fluid F through input end IE of conduit C, wherein the delivered fluid F has one or more conditions that are generally controlled by fluid delivery device 12. For purposes of this method, this disclosure will describe a system where the conditions of fluid F that are controlled by fluid delivery device 12 are temperature and/or velocity but the invention should not be so limited thereby.

At step S104, the temperature of fluid F and workpiece W are generally equalized, or brought into general thermal equilibrium, and the velocity of fluid F delivered into input end IE of conduit C by fluid delivery device 12 is generally maintained at a steady state (i.e., constant velocity and constant temperature).

Method S100 may include a step of measuring one or more conditions of fluid F as it enters input end IE and/or as it egresses output end OE of conduit C of workpiece W, as shown at step S106. As previously described, the one or more conditions may include the temperature of fluid F and the velocity of fluid F. For exemplary purposes, this disclosure will describe a system where sensor 14 measures the egress and exit temperature of fluid while also controlling the temperature and velocity of fluid F as it flows through conduit C.

In an implementation, method S100 also includes a step S108 of mechanically exciting workpiece W and a step of identifying whether an aberration is present within conduit C based on the measured conditions of fluid F S110 as it exits conduit C. In the context of the current example system, the exiting fluid F will exhibit an identifiable variation in one or more conditions (i.e., temperature) when the workpiece is mechanically excited and the step of identifying whether an aberration is present will include a step of correlating such variation change of fluid F temporally with a manual excitation of workpiece W by exciter 16.

In an implementation, the step of exciting workpiece W S106 may include the sub-step of periodically exciting the workpiece W S106 at one or more defined intervals. In some conditions, and to improve reliability, it may be preferable to excite the workpiece W S106 at one or more defined intervals to increase the confidence that measured temperature variations are due to the presence of aberrations and are not a noise artifact or some other anomaly. Under some conditions, using a single excitation cycle may yield inaccurate results because of a low signal to noise ratio of the temperature "signature" of F. However, over a plurality of intervals, due to a fixed temporal relationship with an excitation, it is possible to implement a synchronous detection scheme over many excitation cycles. Lock-in amplifier 19 is one means of accomplishing a synchronous detection scheme over two or more intervals because, by taking multiple samples (N) of temporal fluctuations in F, the signal-to-noise ratio of the temperature signature improves as the square root of N.

Figure 3:
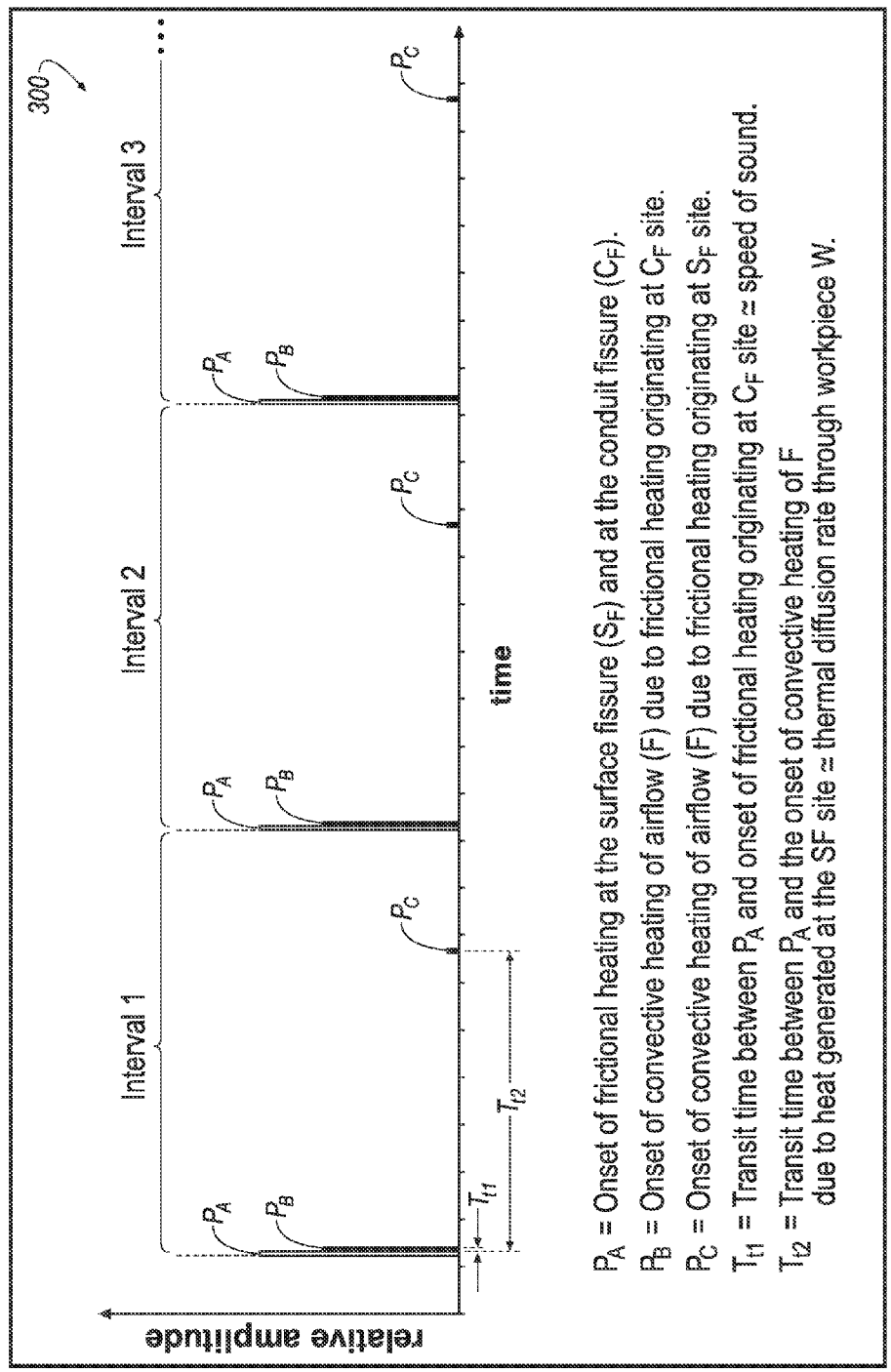
FIG. 3 depicts a chart that illustrates exemplary data relating to detecting aberrations within the conduit of a workpiece, according to an implementation.

Referring now to FIG. 3, an exemplary correlation chart is shown at 300. The x-axis of correlation chart 300 represents time and the y-axis of correlation chart 300 represents a measured relative amplitude of a thermal energy.

The chart includes an excitation event caused by exciter 18 at certain time intervals, which are identified on the chart as Pa. The chart assumes that the onset of Pa at both Sf and Cf sites is simultaneous. The chart also includes temperature variations Pb in the fluid F due to an aberration Cf within conduit C (e.g., such as such as a crack) inasmuch as the aberration will cause frictional heating at the aberration site. As a consequence, the temperature of fluid F will be elevated (i.e., convectively heated) as fluid F passes by the Cf aberration. As shown, the temporal position of peaks Pb are located proximate to the time in which the exciter 16 excites Pa workpiece W. Now, for comparison purposes, the peaks identified as Pc on FIG. 3 represent a temperature variation that may occur in F due to an external surface Sf aberration. First, as illustrated, the relative amplitudes of peaks Pc are much lower than the relative amplitudes of peaks Pb because the heat generated by an external surface Sf aberration will be dissipated as it is conducted through workpiece W toward conduit C. Second, the temporal difference between the Pa and Pc peaks are more separated than that of the Pa and Pb peaks.

Table 1 below illustrates some exemplary transfer times associated with transferring different types of energy through workpiece W made of various materials. The mechanical energy exerted by acoustic energy through exciter 16 transfers at the speed of sound Tt1 through workpiece W. The thermal energy transferred through workpiece W due to an external surface aberration Sf propagates by thermal conduction is much slower Tt2 than that of sound. This relation holds true irrespective of workpiece composition. In view of the stark temporal distinction, processor 18 and/or lock-in amplifier 19 is able to distinguish between aberrations existing within conduit C or external to conduit C.

TABLE 1

| SAMPLE MATERIAL | m/s Speed of sound | m^2/s Thermal diffusivity | $T_{t1}$ Sonic transit time (assumes 3 mm thickness) | $T_{t2}$ Thermal transit time (assumes 3 mm thickness) |
| --- | --- | --- | --- | --- |
| Steel | 6100 | 1.37E−05 | 4.91803E−07 seconds | 9.13E−02 seconds |
| Stainless Steel | 5790 | 3.68E−06 | 5.18135E−07 seconds | 3.39E−01 seconds |
| Hastelloy ® | 5842 | 2.78E−06 | 5.13523E−07 seconds | 4.49E−01 seconds |

In an implementation, processor 18 communicates with lock-in amplifier 19 via bus 23. Lock-in amplifier 19 is a type of phase synchronous detector. Any number of synchronous detectors or synchronous detecting techniques may be employed to duplicate the task accomplished by lock-in amplifier 19. One such synchronous techniques includes signal average over two or more intervals. In an arrangement, processor 18, or in conjunction with lock-in amplifier 19, collects (i) the one or more conditions of fluid F that are measured by sensor 14 versus time, and (ii) the one or more times when exciter 16 excites workpiece W. Processor 18 correlates each of the items as shown in FIG. 3 to identify whether an aberration is present within conduit C of workpiece W. In an implementation, processor 18 may further collect the one or more conditions of fluid F (such as fluid F input temperature) as it enters the input end IE of conduit C.

Now referring to FIG. 3 and Table 1, Tt1 represents the duration between Pa and the onset Pb of conductive heating of fluid F due to frictional heating originating at fissure site Cf Tt2 represents the duration between Pa and the onset of convective heating Pc of fluid F due to frictional heating of fluid F originating at fissure site Sf. Table 1 assumes that the Sf fissure and the Cp fissure are equi-distant from the excitation site 17 of exciter 16. Table 1 also assumes that fissure Sf is 3 millimeters from the proximal wall 24 of conduit C (see distance D in FIG. 1). Table 1 shows for three exemplary workpiece materials there is at least five orders of magnitude difference between, Tt1 and Tt2. This temporal separation between Tt1 and Tt2 can easily be detected by any phase sensitive detection device such as lock-in amplifier 19 and the signal of interest (i.e., Pb) can be easily isolated and measured.

The applied acoustic excitation by exciter 16 will cause nearly instantaneous heating at cracks Cf and Sf. Heat generated at the Cf site along the interior wall will be transferred to the steady state air stream F by convection, and the resulting temperature change will be sensed by the exhaust temperature sensor 20. The lock-in amplifier, which is synchronized to the acoustic excitation period (Interval 1, Interval 2, . . . Interval N), will amplify temperature variations with identical periodicity, and reject all other temperature variations. The air stream F temperature change due to a crack Cf is likely to be small, but unique in its periodicity, so that it may be detected by the lock-in amplifier 19 after sampling and averaging the temperature change over multiple excitation cycles.

For a workpiece (e.g., part of a turbine blade) that is free of interior wall cracks Cf, no substantial synchronous temperature change will be detected. Temperature changes may occur at the outer surface ES due to exterior cracks Sf or at the exciter interface site 17 where the acoustic horn is coupled to the workpiece W. However, unlike internal cracks Cf, which heat the interior conduit wall 24, on the order of 10→seconds, heat from these heating events at the Sf and/or exciter interface site 17 must diffuse through the metal body of the component, so that any resultant heating at the interior wall 24 will be temporally retarded (in time) and diminished (in amplitude) by the diffusion process. Consequently, heating due to inner wall Cf heating can be readily discriminated from outer surface heating, e.g., as a phase offset detected by the lock-in amplifier.

Unless specifically delineated, the steps of the method S100 described above can be performed in any combination and the order of the steps described above or claimed below should not be used to limit the breadth of this disclosure.

Figure 4:
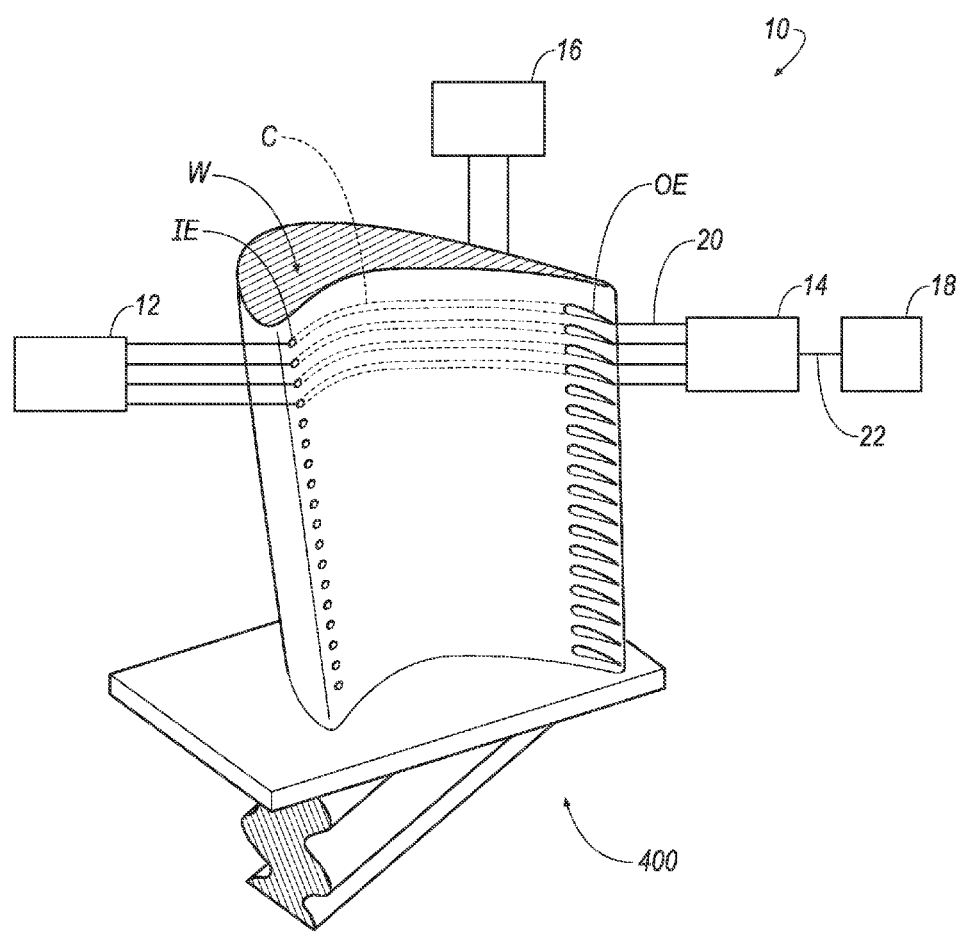
FIG. 4 depicts a system for detecting aberrations within the conduit of a workpiece, according to an implementation.

FIG. 4 depicts a portion of a turbine blade 400 containing a plurality of conduits C. One or more fluid delivery devices 12 are located at the input ends IE of the one or more of the plurality of conduits C and one or more sensors 14 are located at the output ends OE of the one or more of the plurality of conduits C. In the depicted turbine portion, a single fluid delivery device and a single sensor (having multiple input channels) is shown but it is to be appreciated that any number of fluid delivery devices and sensors may be used and the principles hereof should not be so limited thereby. The system and method described herein can be used for detecting aberrations Cf within walls 24 of one or more conduit C of turbine blade 400.

While this specification contains many specifics, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method for detecting a presence of aberrations within a workpiece having internal walls that define an internal conduit of the workpiece, the method comprising:
    delivering fluid through the conduit;
    equalizing the temperature of the workpiece with the temperature of the fluid and maintaining the temperature of the workpiece and the fluid in a steady state condition;
    measuring one or more conditions of the fluid as it traverses at least a portion of the conduit;
    mechanically exciting the workpiece causing an excitement event; and
    identifying whether an aberration is present within conduit or conduit walls based on the one or more measured conditions of the fluid,
    providing a processor having inputs for receiving electronic data reflective of the temperature condition of the fluid and the excitement condition of workpiece, and wherein the identifying step further includes:
    correlating any changes in the temperature condition of the fluid data with the excitement event.

2. A method for detecting a presence of aberrations in a conduit of a workpiece as set forth in claim 1, wherein the correlating step further comprises:
    if the change in temperature is greater than a predefined temperature change, identifying that an aberration is present within the conduit.

3. A method for detecting a presence of aberrations in a conduit of a workpiece as set forth in claim 1, wherein the correlating step further comprises:
    if the change in temperature is greater than a predefined temperature change and the change in temperature occurs within a predetermined time after the onset of the excitement event, identifying that an aberration is present.

4. A method for detecting a presence of aberrations in a conduit of a workpiece as set forth in claim 1, wherein the step of mechanically exciting the workpiece is repeated.

5. A method for detecting a presence of aberrations within a workpiece having internal walls that define an internal conduit of the workpiece, the method comprising:
    delivering fluid through the conduit;
    equalizing the temperature of the workpiece with the temperature of the fluid and maintaining the temperature of the workpiece and the fluid in a steady state condition;
    measuring one or more conditions of the fluid as it traverses at least a portion of the conduit;
    mechanically exciting the workpiece causing an excitement event; and
    identifying whether an aberration is present within conduit or conduit walls based on the one or more measured conditions of the fluid,
    wherein the one or more conditions of the fluid includes a temperature condition, wherein the method further includes:
    providing a processor having inputs for receiving data reflective of the temperature condition of the fluid and data reflective of the excitement event of the workpiece, and wherein the identifying step further includes:
    correlating changes in the temperature condition of the fluid with the data reflective of the excitement event of the workpiece.

* * * * *